United States Patent
Vona et al.

(10) Patent No.: US 6,877,894 B2
(45) Date of Patent: Apr. 12, 2005

(54) SELF-ALIGNING APPARATUS FOR ACOUSTIC THERMOGRAPHY

(75) Inventors: Paul D. Vona, Cocoa, FL (US); Paul J. Zombo, Cocoa, FL (US); Robert E. Shannon, Export, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 0 days.

(21) Appl. No.: 10/253,582

(22) Filed: Sep. 24, 2002

(65) Prior Publication Data

US 2004/0057492 A1 Mar. 25, 2004

(51) Int. Cl.[7] .......................... G01K 11/22; G01K 1/14; G01N 19/00
(52) U.S. Cl. .......................... 374/45; 374/117; 374/57; 374/208
(58) Field of Search .......................... 374/117–119, 45, 374/57, 208, 4; 33/529, 412; 250/334, 341.6, 338.1, 310

(56) References Cited

U.S. PATENT DOCUMENTS

| | | | |
|---|---|---|---|
| 2,302,640 A | * 11/1942 | Schmidt | |
| 3,661,409 A | * 5/1972 | Brown et al. | 285/82 |
| 4,013,905 A | * 3/1977 | Breneman et al. | 310/8.3 |
| 4,140,155 A | * 2/1979 | Tannery | 137/318 |
| 4,255,971 A | * 3/1981 | Rosencwaig | 73/606 |
| 4,676,665 A | * 6/1987 | Twerdochlib | 374/152 |
| 4,690,570 A | * 9/1987 | Wall | 374/188 |
| 4,715,228 A | * 12/1987 | Livsey et al. | 73/640 |
| 5,040,415 A | * 8/1991 | Barkhoudarian | 73/198 |
| 5,044,769 A | * 9/1991 | Kulczyk et al. | 374/137 |
| 5,046,447 A | * 9/1991 | Steinke et al. | 116/217 |
| 5,159,580 A | * 10/1992 | Andersen et al. | 367/132 |
| 5,418,363 A | * 5/1995 | Elings et al. | 250/306 |
| 5,426,341 A | 6/1995 | Bory et al. | |
| 5,450,746 A | * 9/1995 | Howard | 73/105 |
| 5,454,641 A | * 10/1995 | Parker et al. | 374/120 |
| 5,490,810 A | 2/1996 | Hahn et al. | |
| 5,505,416 A | * 4/1996 | Dodge | 248/230.5 |
| 5,525,172 A | 6/1996 | Cadiou | |
| 5,639,972 A | * 6/1997 | Hastings et al. | 73/862.29 |
| 5,770,855 A | * 6/1998 | Fischer | 250/216 |
| 6,006,593 A | * 12/1999 | Yamanaka | 73/105 |
| 6,026,688 A | * 2/2000 | Khuri-Yakub et al. | 73/597 |
| 6,052,911 A | * 4/2000 | Davis | 33/286 |
| 6,100,524 A | * 8/2000 | Yagi et al. | 250/306 |
| 6,108,144 A | 8/2000 | Holderer et al. | |
| 6,112,595 A | * 9/2000 | Stanke et al. | 73/597 |
| 6,173,878 B1 | 1/2001 | Stroh | |
| 6,185,991 B1 | * 2/2001 | Hong et al. | 73/105 |
| 6,200,022 B1 | * 3/2001 | Hammiche et al. | 374/46 |
| 6,213,377 B1 | 4/2001 | Schwerdtle et al. | |
| 6,227,703 B1 | * 5/2001 | DiMatteo et al. | 374/208 |
| 6,236,049 B1 | 5/2001 | Thomas et al. | |
| 6,246,652 B1 | * 6/2001 | Kikukawa et al. | 369/53.38 |
| 6,332,263 B1 | 12/2001 | Schmidt et al. | |
| 6,336,803 B1 | 1/2002 | Funger et al. | |

(Continued)

*Primary Examiner*—Gail Verbitsky

(57) ABSTRACT

An apparatus (10) for performing acoustic thermography including a fixture (32) having a compliant member (40) that allows contacting surfaces of a horn face (20) and a specimen surface (16) to self-align into parallel contact in response to only the contacting force ($F_C$) there between. When the contacting surfaces are brought together in a slightly non-parallel alignment, the contacting force develops a force component ($F_N$) that is normal to the plane of contact. This normal force causes deflection of a compliant member, thereby providing movement that brings the contacting surfaces into parallel alignment. The compliant member may be a spring (48), elastomer (50), swivel member (56), bearing member (80), or a curved non-stick surface (90) in various embodiments.

18 Claims, 3 Drawing Sheets

U.S. PATENT DOCUMENTS

| | | |
|---|---|---|
| 6,343,495 B1 | 2/2002 | Cheppe et al. |
| 6,371,429 B1 * | 4/2002 | Gillespie ................. 248/354.1 |
| 6,399,948 B1 | 6/2002 | Thomas et al. |
| 6,406,769 B1 | 6/2002 | Delabre |
| 6,430,324 B1 * | 8/2002 | Muramatsu et al. .......... 385/12 |
| 6,437,334 B1 | 8/2002 | Thomas et al. |
| 6,487,515 B1 * | 11/2002 | Ghoshal ..................... 702/136 |
| 6,513,385 B1 * | 2/2003 | Han et al. ..................... 73/629 |
| 6,561,473 B1 * | 5/2003 | Ianello .................... 248/219.4 |
| 6,594,869 B1 * | 7/2003 | Chen ........................ 24/274 R |
| 6,781,125 B2 * | 8/2004 | Tokuda et al. .............. 250/310 |
| 2002/0050565 A1 * | 5/2002 | Tokuda et al. .............. 250/310 |
| 2002/0076184 A1 * | 6/2002 | Iyoki ......................... 385/123 |

* cited by examiner

SELF-ALIGNING APPARATUS FOR ACOUSTIC THERMOGRAPHY

FIELD OF THE INVENTION

This invention relates generally to the field of acoustic thermography and more particularly to a self-aligning fixture for providing contact between a test specimen and the horn of an acoustic thermography system.

BACKGROUND OF THE INVENTION

There are many known methods for nondestructively examining a test specimen. Many of these methods involve introducing energy into the specimen and detecting a modified form of that energy as it leaves the specimen. For example, it is known to apply X-ray, ultrasonic, magnetic, or heat energy into a test specimen and to detect flaws in the specimen as perturbations in the respective energy pattern as it returns from the specimen.

Acoustic thermography is one such form of nondestructive examination that involves the application of acoustic energy to a test specimen and the measurement of heat energy that is generated within the specimen as a result of the acoustic energy interacting with a crack. As sound energy passes through the material of a specimen, opposing surfaces of a crack or other flaw are caused to rub together, thus generating heat. Because undamaged areas of the specimen are only minimally heated by the acoustic waves, a thermal image of the specimen will reveal the flawed area as having as exhibiting an increase in temperature.

The effectiveness of an acoustic thermography examination is directly related to the efficiency of the input of acoustic energy into the test specimen. U.S. Pat. No. 6,236,049 describes the need for a coupler between the acoustic transducer the test specimen in order to couple about 30 to 40 percent of the ultrasonic energy produced by the transducer into the specimen. U.S. Pat. No. 6,399,948 describes an acoustic thermography system that delivers the acoustic energy to the specimen through an electromagnetic acoustic transducer (EMAT), thereby providing coupling to the specimen without the need for mechanical contact.

SUMMARY OF THE INVENTION

The need remains for an improved mechanical coupling between the acoustic transducer and the test specimen during an acoustic thermography examination.

An apparatus for nondestructive testing is described herein as including: an acoustic energy source comprising a probe face for delivering acoustic energy to a surface of a specimen; a fixture for transmitting a contact force between the probe face and the specimen surface, the contact force comprising an axial component perpendicular to the specimen surface and a normal component parallel to the specimen surface; the fixture further comprising a compliant member responsive to the normal component of the contact force to position the probe face and the specimen surface into parallel contact; and a thermal imaging apparatus for generating an image responsive to a temperature profile of the specimen under influence of the acoustic energy. The compliant member is responsive to the normal component force applied on the specimen surface or to the normal component force applied on the probe face. The compliant mount may be a spring, an elastomer, or a non-stick surface of a specimen gripping face.

The apparatus may include: a clamp connected to the specimen; an anchor plate; a plurality of bolts each having a first end connected to the clamp and a second end extending through a respective opening formed in the anchor plate; and a compliant mount connected between the second end of each respective bolt and the anchor plate. The apparatus may include: a clamp connected to the specimen; and a swivel member connecting the clamp to a base for resisting the contact force, the swivel member permitting relative movement between the acoustic energy source and the specimen in response to the normal component of the contact force for aligning the probe face and the specimen surface into parallel contact. The apparatus may include: a ring member rotatably connected about a first axis to the base; and a clamping member rotatably connecting the specimen to the ring member about a second axis perpendicular to the first axis. The apparatus may include: a clamp connected to the specimen; an outer shell connected to a base; an inner shell connected to the clamp and disposed within the outer shell; and a bearing member supporting the inner shell within the outer shell for transmitting the contact force while permitting relative movement between the clamp and the base in response to the normal component of the contact force.

The compliant member may further include a gripping member allowing rotation of the specimen within the fixture while transferring the contact force. The gripping member may further include a curved surface for contacting the specimen.

An apparatus for nondestructive testing is described herein as including: an energy source comprising a probe face for delivering energy to a surface of a specimen; a means for exerting a contact force between the probe face and the specimen surface; a means responsive to the contact force for positioning the probe face and the specimen surface into parallel contact; and a sensing apparatus for generating a signal responsive to a condition of the specimen under influence of the energy. The means for positioning may include a spring, an elastomer, a swivel member, a bearing member, a specimen-gripping member comprising a non-stick surface, or a specimen-gripping member allowing rotation of the specimen relative to the specimen gripping member while transferring the contact force. The specimen-gripping member may be a curved gripping face.

In an apparatus for imparting acoustic energy into a specimen for performing a nondestructive examination of the specimen, the apparatus including a fixture for transmitting a contact force between an acoustic energy source probe tip face and a specimen surface, an improvement is described herein as including a compliant member providing a range of motion responsive to a component of the contact force for aligning the probe tip face and the specimen surface into parallel contact.

BRIEF DESCRIPTION OF THE DRAWINGS

These and other advantages of the invention will be more apparent from the following description in view of the drawings that show.

DETAILED DESCRIPTION OF THE INVENTION

Figure 1:
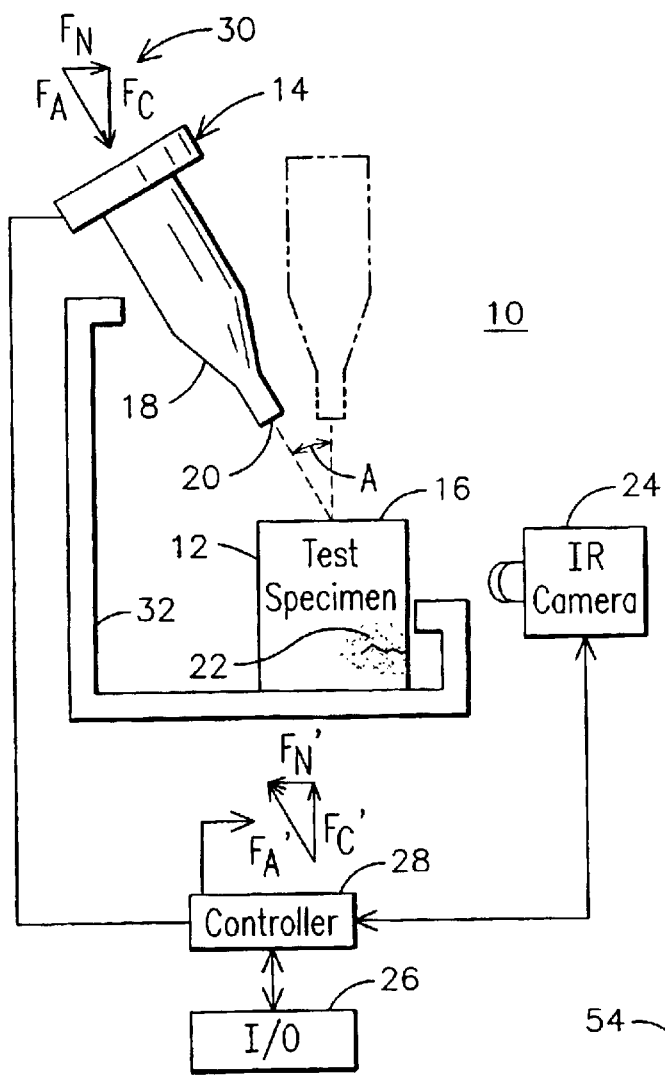
FIG. 1 is a schematic diagram of a system for performing acoustic thermography.

A system 10 used for nondestructive testing of a test specimen 12 is illustrated in schematic form in FIG. 1. The system includes an acoustic energy source 14 for delivering acoustic energy to a surface 16 of the specimen 12. The acoustic energy source 14 may be an ultrasonic piezoelectric device. One such acoustic energy source 14 is sold under the name Branson 2000 series ultrasonic assembly system or Thermosensorik GmbH thermographic inspection system. The acoustic energy is transferred through a probe tip such as horn 18 having a face 20 for making contact with specimen surface 16. Vibrations within the specimen 12 will cause localized heating in an area 22 surrounding a crack in the specimen 12. The increased temperature of area 22 is detected by a thermal imaging apparatus 24 for generating an image responsive to a temperature profile of the specimen 12 under influence of the acoustic energy. The image may be displayed on an input/output device 26 such as a personal computer. A controller 28 is used to control the operation of the various components of the system 10.

In order to transfer the acoustical energy from the acoustic energy source 14 to the specimen 12, it is necessary to apply a force between the probe tip face 20 and the test specimen surface 16. This may be accomplished by using an actuator provided by the ultrasonic source manufacturer or any commercially available power source such as a mechanical, hydraulic or pneumatic press, represented by force diagram 30, connected to either the horn 18 or test specimen 12, with the other of the two being supported firmly against a base. In order to maximize the efficiency of the acoustical energy transfer, it is desired to position probe face 20 and specimen surface 16 into parallel contact. Even a small misalignment of these two contact surfaces will significantly affect the results of the inspection of specimen 12. Horn 18 is illustrated in FIG. 1 in a grossly misaligned position, with its properly aligned position being illustrated in phantom. In reality, it is generally quite easy to align the two contact surfaces 16, 20 to a near-parallel position. However, to obtain optimal results with parallel contact there between, a very precise alignment of horn 18 and specimen 12 is required, preferably with zero gap between the contact surfaces.

The system 10 of the present invention utilizes a fixture 32 that is specially adapted to be self-aligning to position the probe face 20 and specimen surface 16 into parallel contact. This is accomplished by using a component of the contact force exerted between the acoustic energy source 14 and the specimen 12 as the motive force for positioning one or both of the two contact surfaces 16, 20. As can be seen in FIG. 1, contact force $F_C$ has two components: an axial component $F_A$ along an axis of the horn 18 and perpendicular to the specimen surface, and a normal component parallel to the specimen surface 16 and perpendicular to the axis of the horn 18. These two components occur when the probe face 20 contacts the specimen surface 16 in an off-parallel angle, resulting in essentially point contact between the two surfaces with perhaps some local deformation resulting in a small area contact. Because of the angle of contact A, the axial force $F_A$ is resolved into components normal to and parallel with the surface 16. The normal component $F_N$ has a significantly smaller magnitude than the axial component $F_A$ but is illustrated in exaggerated proportions in FIG. 1 for purposes of illustration. If the two surfaces 16, 20 were in perfect parallel contact, the normal component would be zero and the entire contact force would be exerted along the axis of the horn 18. However, in a real world situation, there will be a small misalignment between the two opposed contact surfaces 16, 20. Angle A in a real world situation will likely be less than one degree (0.0175 rad). For a typical setup of a fixture 32 with normal manufacturing tolerances, the normal component $F_N$ may be approximately two percent of the contact force $F_C$. A typical contact force $F_C$ may be 50–150 pounds, for example, so the normal component may be a force of less than one pound.

Figure 2:
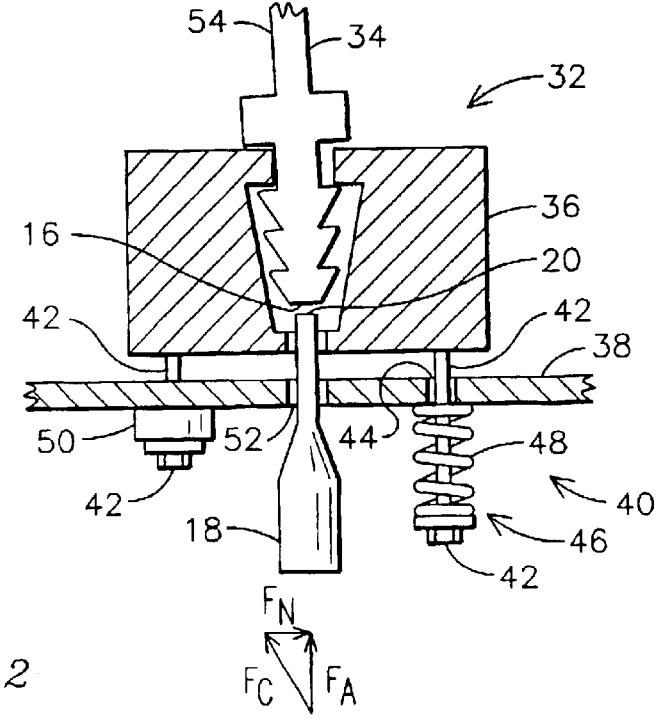
FIG. 2 is a partial cross-sectional view of a fixture having a compliant mount used for acoustic thermography.

FIG. 2 illustrates one embodiment of a fixture 32 self-aligning to position the probe face 20 and specimen surface 16 into parallel contact. The specimen being examined in FIG. 2 is a turbine blade 34. A clamp 36 releasably grips blade 34. Clamp 36 is connected to a fixed base in the form of anchor plate 38 by a compliant member 40. Compliant member 40 includes a plurality of bolts 42 having a first end connected to clamp 36 and a second end extending through a respective opening 44 formed in the anchor plate 38. A compliant mount 46 is attached between the bolt 42 and the anchor plate 38. Two alternative embodiments of compliant mount 46 are illustrated in FIG. 2; a spring 48 and an elastomer 50 such as rubber. In a typical installation a single type of compliant mount 46 may be used, however, two embodiments are shown in FIG. 2 for purposes of illustration. The component parts of the compliant member 40 are selected to provide a predetermined stiffness for permitting relative movement between the specimen surface 16 and the probe face 20 in response to the normal component $F_N$ of the contact force $F_C$ for aligning the probe face 20 and the specimen surface 16 into parallel contact. In the embodiment of FIG. 2, the horn 18 is inserted through an opening 52 in anchor plate 38 to make contact with blade 34. A slight non-parallelism between the two contact surfaces 16, 20 will generate a normal component $F_N$ of contact force $F_C$, thereby resulting in a deformation of compliant member 40. As the degree of the non-parallelism between surfaces 16, 20 increases, the magnitude of the normal component force $F_N$ will also increase, thereby increasing the deflection of compliant member 40. While FIG. 2 illustrates the use of a compliant member 40 connected to the clamp 36 to allow the specimen surface 16 to move in response to the normal force component $F_N$, it may be appreciated that the same concept may be applied by having a compliant member connected to a clamp engaged with the horn to provide for a self-aligning movement of the probe face in response to the normal component of the contact force. Furthermore, any of the component parts in the load path between the blade 34 and the anchor plate 38 may provide the necessary compliance.

Note that the construction of fixture 32 allows the normal component force $F_N$ to move the specimen surface 16 in a direction that corrects the non-parallelism because the point of contact between the two opposed surfaces 16, 20 is suspended beyond the location of the compliant member 40 when viewed in the direction of force in the horn 18. (i.e. the point of contact is above the support plate 38 in FIG. 2 where the direction of force in the horn 18 is toward the top of the page) Assuming that the airfoil portion 54 of blade 34 is leaning left as illustrated in the embodiment of FIG. 2, the normal force $F_N$ will be exerted toward the right side of FIG. 2 at the specimen surface 16. This will create a clockwise moment of inertia about the specimen surface 16 that will result in the airfoil portion 54 of blade 34 moving to the right in FIG. 2 due to the deflection of compliant mounts 46, thereby placing the two opposed contact surfaces 16, 20 into a parallel or more nearly parallel position.

Figure 3:
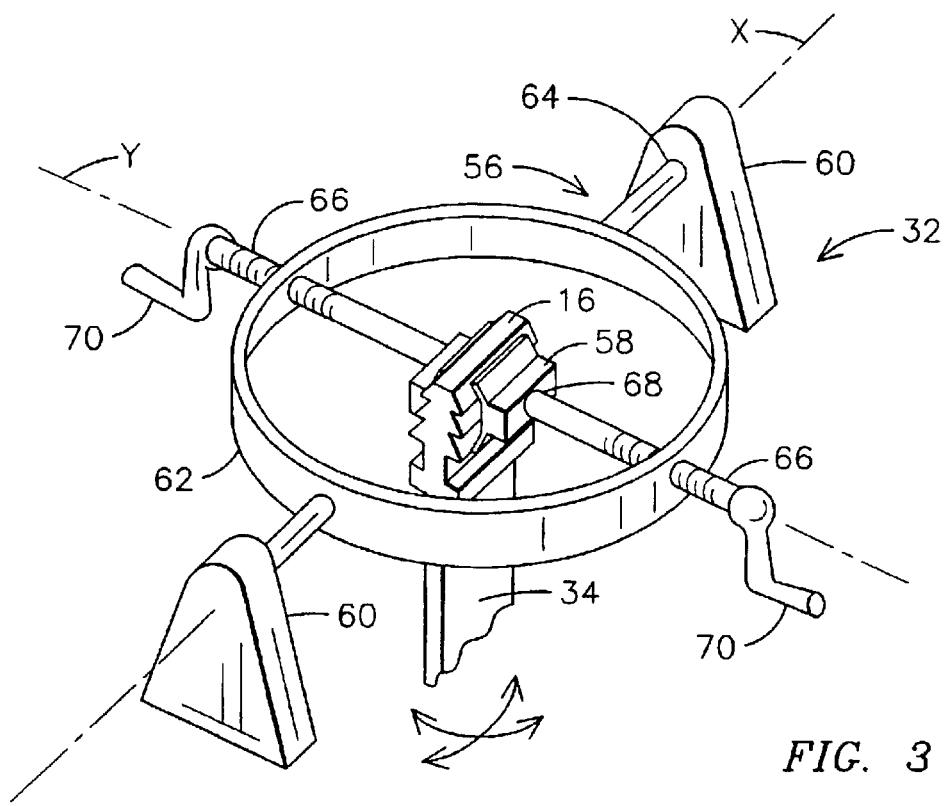
FIG. 3 is a partial cross-sectional view of a fixture having a swivel used for acoustic thermography.

FIG. 3 illustrates a further embodiment of fixture 32 wherein the compliant member 40 takes the form of a swivel member 56. A clamp 58 releasably grips the specimen turbine blade 34. Clamp 58 may be formed of a suitable metal or polymer material, for example aluminum or nylon, to provide the necessary load bearing capability without causing damage to the blade 34. The swivel member 56 connects the clamp 58 to a fixed base 60 for resisting the contact force $F_C$ that would be applied by a horn (not shown) projecting downward onto a top specimen surface 16. Swivel member 56 includes a ring member 62 rotatably connected about a first axis X to the base 60. Ring member 62 is illustrated as having a generally circular shape, although one skilled in the art will appreciate that other shapes such as square or rectangular may be used in other applications. The swivel connection 64 allowing rotation of the ring member 2 relative to the base 60 may be any type of low friction connection known in the art, such as a ball-in-socket or pin-in-cone connection. The clamp 58 is rotatably connected to the ring member 62 about a second axis Y perpendicular to the first axis X. A pair of opposed rods 66 that are threaded into mating threaded holes formed in ring member 62 provides this connection. The rods 66 engage clamp 58 at swivel connection 68 consisting of a generally pointed end of rod 66 and a mating depression in clamp 58. Handles 70 on the remote ends of the rods 66 allow the rods to be rotated to urge clamp 58 together to grip blade 34. Swivel member 56 of the fixture 32 of FIG. 3 provides a range of motion along axes X,Y as indicated by the arrows. A contact force $F_C$ exerted by a non-parallel probe face (not shown) onto the specimen surface 16 will create a normal component $F_N$ as a result of the non-parallelism between the mating surfaces. Depending upon the direction of the normal component, it will induce the rotation of the specimen surface 16 about one or both axes X,Y, thereby placing the specimen surface 16 and the probe face 20 in parallel contact. The contact force drives this self-aligning function without the need for the application of an additional force and without the need for a precise mechanical alignment adjustment by the operator.

Figure 4:
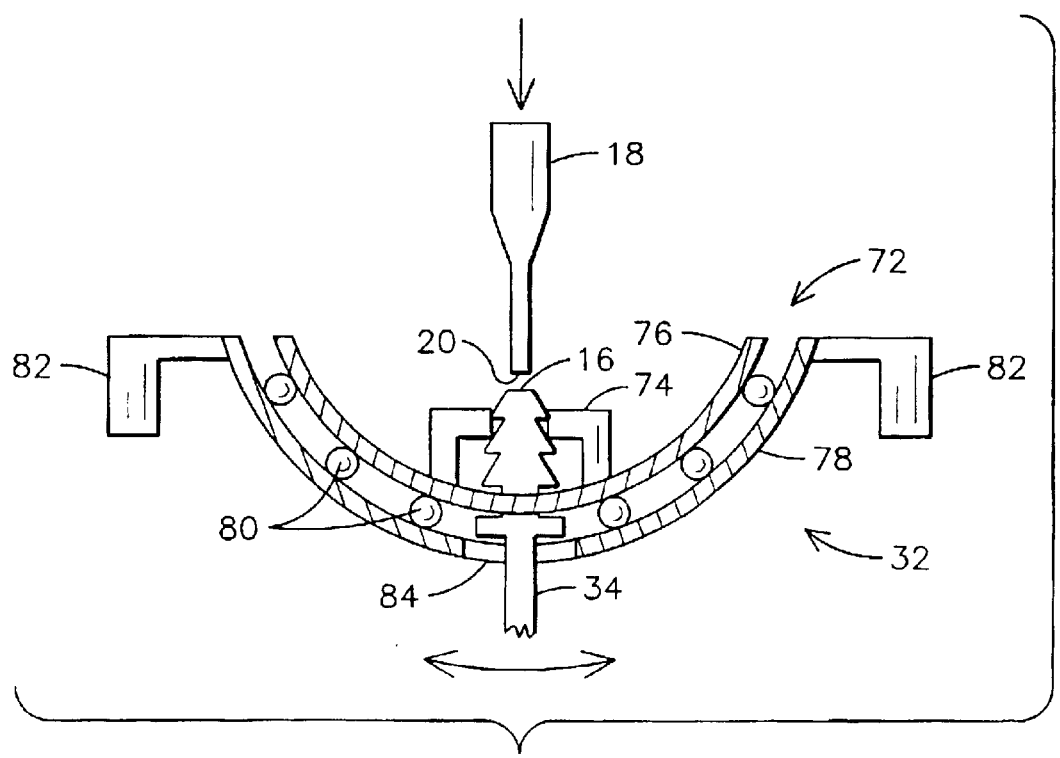
FIG. 4 is a partial cross-sectional view of a fixture having a bearing used for acoustic thermography.

A further embodiment of a fixture 32 for use during an acoustic thermography examination is illustrated in FIG. 4. Fixture 32 includes a compliant member in the form of a bearing member 72. A turbine blade 34 is gripped by a clamp 74 that is connected to an inner shell 76. Inner shell 76 is rotatably supported within an outer shell 78 by a bearing member 80 of any style known in the art, such as ball bearings, roller bearings, a bearing surface of a lubricating material, etc. Outer shell 78 is fixedly connected to a base member 82. The blade 34 extends through an opening 84 formed in the outer shell 78 to allow it a range of motion as indicated by the arrow. One may appreciate that the range of motion of the bearing member 80 also extends into and out of the plane of the page of FIG. 4. If opposing contact surfaces 16, 20 are not parallel, a normal component $F_N$ will be developed at the specimen surface 16 that will cause the inner shell 76 to rotate within the outer shell 78. In this manner, bearing member 80 permits relative movement between the clamp 74 and the base 82 in response to the normal component $F_N$ of the contact force $F_C$.

Figure 5:
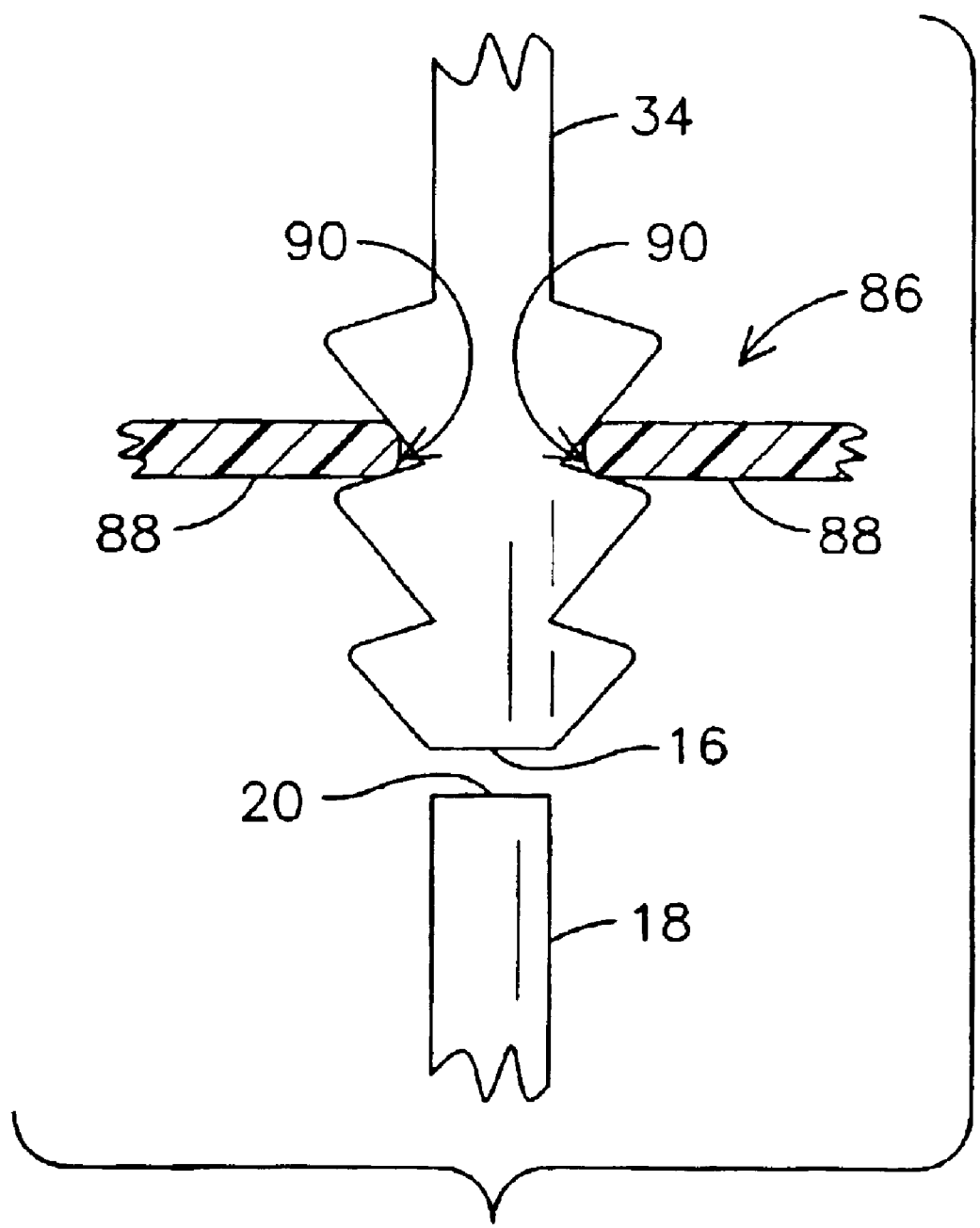
FIG. 5 is plan view of a turbine blade being held in a clamp during an acoustic thermography inspection.

FIG. 5 illustrates an embodiment wherein the desired degree of compliance is provided through the design of the clamping member used to secure the component being tested. A blade 34 is urged against the face 20 of horn 18 by clamp 86. Clamp 86 includes opposed gripping members 88 having respective gripping faces 90 for making contact with the blade 34. Each gripping face 90 is shaped to allow rotation of the blade 34 within the clamp 86 while the clamp 86 is transferring the contact force. In this manner, a small misalignment of contact faces 16, 20 which produces a moment force about clamp 86 will result in a small rotation of the blade 34 within clamp 86 and self-alignment of the two contact faces 16, 20. In the embodiment of FIG. 5, the gripping faces 90 are curved in cross-section and they make line contact with blade 34 to permit the rotation of blade 34 without interfering obstruction. Selecting the material of construction of gripping members 88 to be somewhat compliant and/or to have a low surface coefficient of friction may enhance such compliance. For example, gripping members 88 or gripping faces 90 may be constructed of a polymer such as nylon and/or may include a non-stick surface coating, such as PTFE, carbon black or other known lubricant.

While the preferred embodiments of the present invention have been shown and described herein, it will be obvious that such embodiments are provided by way of example only. Numerous variations, changes and substitutions will occur to those of skill in the art without departing from the invention herein. Commonly available materials such as steel, aluminum or plastic may be used to manufacture all of the illustrated components using standard manufacturing processes. Accordingly, it is intended that the invention be limited only by the spirit and scope of the appended claims.

We claim as our invention:

1. An apparatus for nondestructive testing, the apparatus comprising:

an acoustic energy source comprising a probe face for delivering acoustic energy to a surface of a specimen;

a fixture comprising a fixed base and a gripping mechanism holding the specimen relative to the fixed base to resist a contact force exerted by the probe face directly onto the specimen surface, the contact force comprising an axial component perpendicular to the specimen surface and a normal component parallel to the specimen surface, direct contact between the probe face and the specimen surface initially being point contact due to a non-parallel alignment of the probe face and the specimen surface;

the fixture further comprising a compliant member not disposed between the probe face and the surface of the specimen and responsive only to the normal component of the contact force to rotate the gripping mechanism relative to the fixed base to position the probe face and the specimen surface into parallel direct contact to increase transmission of the acoustic energy there between relative to energy transmission though the point contact; and a thermal imaging apparatus for generating an image responsive to a temperature profile of the specimen under influence of the acoustic energy.

2. The apparatus of claim 1, wherein the compliant member comprises a compliant mount having a predetermined stiffness.

3. The apparatus of claim 2, wherein the compliant mount comprises a spring.

4. The apparatus of claim 2, wherein the compliant mount comprises an elastomer.

5. The apparatus of claim 1, further comprising:

the gripping mechanism comprising a clamp connected to the specimen;

the fixed base comprising an anchor plate;

a plurality of bolts each having a first end connected to the clamp and a second end extending through a respective opening formed in the anchor plate; and the compliant member comprising a compliant mount connected between the second and of each respective bolt and the anchor plate.

6. The apparatus of claim 1, further comprising:

the gripping mechanism comprising a clamp connected to the specimen; and a swivel member connecting the damp to the fixed base for resisting the contact force, the swivel member permitting relative movement between the acoustic energy source and the specimen in response to the normal component of the contact force for aligning the probe face and the specimen surface into parallel contact.

7. The apparatus of claim 6, further comprising:

the swivel member further comprising a ring member rotatably connected to the fixed base about a first axis of rotation; and the gripping mechanism rotatably connecting the specimen to the ring member about a second axis of rotation perpendicular to the first axis.

8. The apparatus of claim 1, further comprising:

the gripping mechanism comprising a clamp connected to the specimen;

an outer shell connected to the fixed base;

an inner shell connected to the clamp and disposed within the outer shell; and a bearing member supporting the inner shell within the outer shell for transmitting the contact force while permitting relative movement between the clamp and the base in response to the normal component of the contact force.

9. The apparatus of claim 1, wherein the compliant member comprises a non-stick surface of the gripping mechanism.

10. The apparatus of claim 1, wherein the compliant member further comprises a gripping member allowing rotation of the specimen within the fixture while transferring the contact force.

11. The apparatus of claim 10, wherein the gripping member further comprises a curved surface for contacting the specimen.

12. An apparatus for nondestructive testing, the apparatus comprising:

an energy source comprising a probe face for delivering energy directly onto a surface of a specimen;

a means for exerting a contact force between the probe face and the specimen surface;

a means responsive to the contact force for providing relative rotation between the probe face and the specimen surface to position the probe face into direct parallel contact with the specimen surface, the means for providing relative rotation not having any member disposed between the probe face and the specimen surface; and a sensing apparatus for generating a signal responsive to a condition of the specimen under influence of the energy, wherein the means for providing relative rotation comprises a specimen gripping member allowing rotation of the specimen relative to the specimen gripping member while transferring the contact force.

13. The apparatus of claim 12, wherein the means for providing relative rotation comprises a spring.

14. The apparatus of claim 12, wherein the means for providing relative rotation comprises an elastomer.

15. The apparatus of claim 12, wherein the means for providing relative rotation comprises a swivel member.

16. The apparatus of claim 12, wherein the means for providing relative rotation comprises a bearing member.

17. The apparatus of claim 12, wherein the means for providing relative rotation comprises a specimen gripping member comprising a non-stick surface.

18. The apparatus of claim 12, wherein the specimen gripping member comprises a curved gripping face.

* * * * *